United States Patent [19]

Krasberg

[11] 4,430,988

[45] Feb. 14, 1984

[54] HEATING OF UNDERWATER EQUIPMENT

[76] Inventor: Alan Krasberg, 24 Devanha Gardens, Aberdeen, AB1 2UU, Scotland

[21] Appl. No.: 240,409

[22] Filed: Mar. 4, 1981

[51] Int. Cl.³ .............................................. A61F 7/00

[52] U.S. Cl. .................................... 126/206; 126/263

[58] Field of Search ................ 126/204, 206, 208, 263

[56] References Cited

U.S. PATENT DOCUMENTS 3,599,625 8/1971 Curtis ................................ 126/204

3,884,216 5/1975 McCartney ......................... 126/204

4,237,865 12/1980 Lorenz ............................... 126/429

*Primary Examiner*—Ronald C. Capossela

*Attorney, Agent, or Firm*—Gerald J. Ferguson, Jr.; Joseph J. Baker

[57] ABSTRACT

The heating of submersible hulls, diving suits and other underwater equipment usually involves use of electrical batteries. However, in cold water operations these electrical batteries prove quite inadequate for the task. The invention provides for a self-contained heating system involving the bringing together in a submerged reaction zone of substances capable of reacting together exothermically. Preferably one of the substances is a metal e.g. aluminium in ingot form, and the other substance is an aqueous solution of sodium hydroxide and is fed to the ingots of aluminium. The invention is also apparatus for carrying out the reaction and transferring the heat generated.

20 Claims, 2 Drawing Figures

HEATING OF UNDERWATER EQUIPMENT

Figure 1:
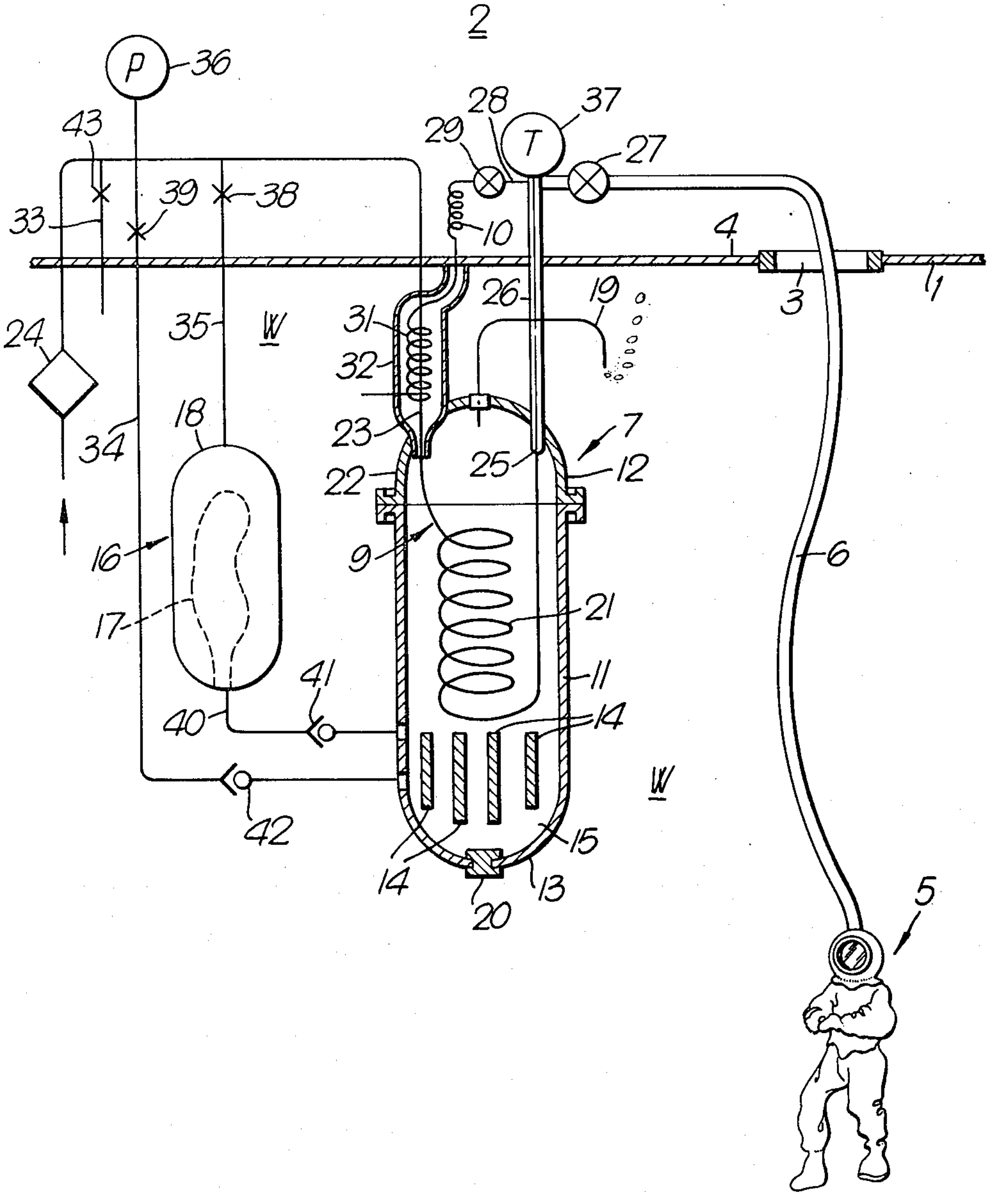

This invention relates to the heating of underwater equipment such for example as hot-water diving suits and submersible hulls used in diving operations.

There exists a need for a simple, safe and efficient autonomous underwater source of heat for use in heating divers working in the water and/or for use in heating the interior of submersible hulls such, for example as submarines, submersibles, diving bells and hyperbaric evacuation chambers. Thus, the comfort and even survival of an operator for any length of time in the pressurized helium-oxygen atmosphere of a submerged hull depends on maintaining relatively high gas temperatures, as the thermal conductivity of this gas is extremely high compared to sea-level air.

For some time now the heat source used in heating such equipment has been an electrical battery system. However, with the present increasing use of submersible hulls (so-called diver lock-out submersibles) as a base for cold-water operations, such a heat source is quite inadequate for the task. That is, there is at present no satisfactory method of heating the divers on an autonomous operation, or for maintaining the lock-out compartment temperature at an adequate level for any length of time if for some reason the submersible cannot be recovered immediately. As one of these submersibles typically carries 40 kW-hours of batteries in toto, use of these batteries to heat water to be passed to the diving suit in the open-circuit technique is obviously not feasible. Various substitutes have been tried, among them electrically-heated suits and closed-circuit hot-water suits (sometimes coupled with a heat pump to further increase the efficiency). These methods have the disadvantage of being complicated and delicate, and the result is that there is a lowering of output of productive work by the diver.

The object of the invention is to provide for the generation of heat under water in such a manner that the aforesaid difficulties are obviated or mitigated.

According to the present invention a method of generating heat at an underwater location comprises bringing together in a submerged reaction zone substances capable of reacting together exothermically. Preferably the substances are respectively liquid and solid substances. More preferably one of the substances is a metal.

Most preferably the metal is aluminium and the reactant is an aqueous solution of sodium hydroxide, the exothermic reaction being:

$$2Al+2NaOH+2H_2O\rightarrow 2NaAlO_2+3H_2.$$

Advantageously aluminium is in ingot form.

Said reaction yields about 93 k-cal of heat per gram molecule, or about $2\frac{1}{2}$ kW of heat energy per pound of aluminium.

By virtue of the invention autonomous underwater heat is produced with well over $1\frac{1}{2}$ orders of magnitude more power per unit of volume or mass than is possible with lead-acid batteries. Thus, suitably sized heat-generating means associated with a submersible would provide ample heat for hours of open-circuit diving-suit heating, and also heating backup in the lock-out compartment of the submersible for a considerable time in the event that a problem arose. Said heat-generating means also of course frees the usual electric battery system of the submersible for tasks more suitable for it, such as the driving of motors, pumps and electrical systems.

Further according to the present invention I provide submersible apparatus for use in underwater operations, comprising a hull to house personnel, heat generating means associated with the hull including (a) a reaction chamber having therein a reaction zone for substances capable of reacting together exothermically and (b) dispensing means for liquid reactant connected to the reaction chamber to enable feeding of liquid reactant to the reaction zone.

In a preferred apparatus a venting tube extends from the top of the reaction chamber to discharge into the ambient water, and in the bottom portion of the reaction chamber there is an aperture which has a disc or valve for opening the aperture at a predetermined temperature to enable entry of water to the reaction zone or dumping of the contents on temperature runaway, the water being sucked through the aperture by the "air-lift" effect of gas exiting through the venting tube.

Preferably the dispensing means for a liquid reactant include an accumulator of the separated type adjacent to the reaction zone chamber, one side being connected to the water supply ducting and the other for the liquid reactant being connected to the reaction chamber so that pressurised water in the one side compresses the other to force the liquid reactant into the reaction zone.

More preferably the accumulator is a jacket and bladder accumulator.

Preferably also the apparatus includes liquid heating means having a heat exchanger in the reaction chamber.

Most preferably the heat-generating means are on the hull exteriorly thereof, and the heating means include a pump for location in the cold water outside the hull, supply ducting extending from the pump through the hull interior to the heat-exchanger inlet, and discharge ducting extending from the heat-exchanger outlet into the hull interior.

Preferably also the discharge ducting includes a stand pipe extending upwards from the heat-generating means and into the hull and connectible at its upper end, to the upper end of a diver's hose to enable use of the heated water to heat a diving suit.

The preferred apparatus further includes a branch pipe extending from the supply ducting in the hull to the hull exterior, and has a valve in the branch pipe to enable adjustment of the head pressure and water flow through the heating system. Advantageously this apparatus also has a branch pipe extending from the supply ducting in the hull to the reaction zone in the reaction chamber and has a valve in the branch pipe to enable the introduction of cold water to the reaction zone so that the reaction is dampened and simultaneously combustion products are forced from the reaction chamber through the venting tube.

The apparatus may include a water radiator in the hull, a water supply line extending from the discharge ducting to the radiator inlet, and a water exhaust line extending from the radiator outlet and through the hull to discharge into the ambient water.

The water exhaust line may be a heat exchanging helical coil, which encloses a portion of the supply ducting extending between the hull and the heat-exchanger inlet and has a heat-insulating housing mounted on the reaction chamber and enclosing the helical coil.

Preferably the reaction chamber is of upright generally cylindrical form with the reaction zone in the lower portion thereof, and the heat exchanger is an upright helical tube disposed in the chamber above the reaction zone.

In an equally preferred but modified embodiment of the apparatus of the present invention the heat generating means are in the interior of the hull, the reaction chamber and the hull abut one another, and the area of abutment forms a heat-conductive partition to enable heat-transfer to the hull interior.

In this modified embodiment the reaction chamber and the hull may be contained within a common insulating layer.

Preferably the reaction heat from the reaction chamber in the modified embodiment is conducted via the heat conductive partition to a finned heat exchanger on the interior surface of the hull.

Figure 2:
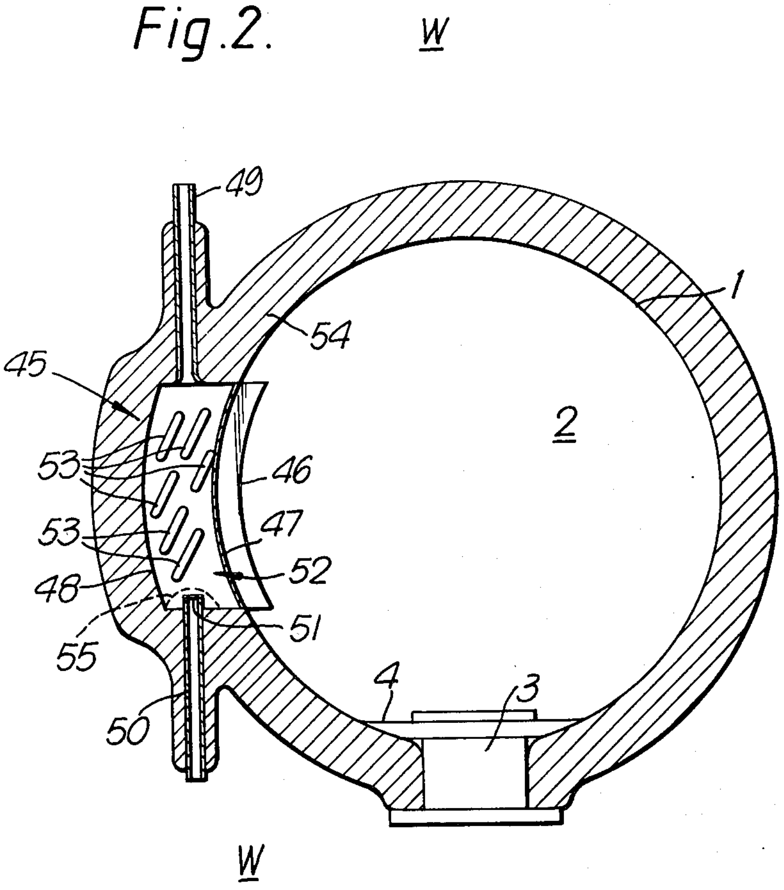

Embodiments of the invention will be described by way of example with reference to the accompanying diagrammatic drawings in which;

FIG. 1 and FIG. 2 are fragmentary sectional side views of submersible apparatus for use in cold-water diving operations.

Referring to FIG. 1 of the drawings:

The apparatus consists of (a) a hull 1 having therein a diver lock-out compartment 2 with an opening 3 in the floor 4 thereof for passage of a diver fitted with an open-circuit water-heated diving suit 5 fed by a length of heat-insulated water hose 6 passing through the opening 3 (b) heat-generating means 7 mounted on the floor 4 of the compartment 2 adjacent to the floor opening 3 and extending exteriorly of the hull 1 and (c) heat-exchanging means including water tubing 9 extending through the heat-generating means 7 and connected to the diver's hose 6 and to a hot-water radiator 10 in the compartment 2.

The heat-generating means 7 include exteriorly of the hull 1 and mounted thereon a heat-insulated reaction chamber 11 in the form of an upright cylinder with a domed top end 12 and a domed bottom end 13, ingots 14 of aluminium in a reaction zone 15 formed by the lower end portion of the reaction chamber 11, and a jacket-and-bladder type accumulator 16 disposed alongside the reaction chamber 11 and connected thereto to dispense a stored, aqueous solution of sodium hydroxide (47% NaOH) as reactant by passing same into contact with the aluminium in the reaction zone 15, an accumulator bladder 17 storing the reactant solution and being compressible by pressurized water fed to an accumulator jacket 18 to force the reactant solution into the reaction zone 15 through a tube 40 and a check valve 41. A short, open length of stainless steel venting tube 19 extends from the top end 12 to release gaseous reaction products from the reaction chamber 11 into the ambient water W. A large central safety feed-through opening in the bottom end 13 is closed by a disc 20 which melts at a critical temperature (in the order of 190° F.)

The water tubing 9 of the heat-exchanging means include an upright helical coil 21 of water tubing within the upper portion of the reaction chamber 11 for contact by the products of combustion rising from the reaction zone 15. The ends of the coil 21 are disposed at the top of the chamber 11, the inlet end 22 of the coil being connected to one end of a manifold water supply pipe 23 of stainless steel extending within the compartment 2, and an immersed sea-water pump 24 delivering about 1.7 gal/min being connected to the other end of the manifold supply pipe 23 through the floor 4 of the compartment. The outlet end 25 of the coil 21 is connected to the inlet end of the diver's hose 6 through a heat-insulated stand pipe 26 penetrating the floor 4 of the compartment 2 and having at the top thereof a shut-off valve 27 controlling the flow to the diver. A branch pipe 28 with a needle valve 29 therein connects the top of the stand pipe 26 to the radiator 10 within the compartment 2, and a heat-exchanging outlet pipe 31 from the radiator 10 is coiled around an exterior downstream end portion of the manifold pipe 23 to transfer heat to the entering water, and discharges into the ambient water W, the coiled outlet pipe 31 being enclosed by an insulating housing 32 mounted on the chamber 11 exteriorly thereof and capable of withstanding external pressure. The manifold pipe 23 has three valve-controlled branch pipes opening therefrom, the first 33 extending through the floor 4 into the ambient water W and having therein a by-pass valve 43 to provide for adjustment of head pressure and flow through the system, the second 34 extending through the floor 4 to the bottom of the reaction chamber 11 to discharge water into the reaction zone 15, through a check valve 42 and thereby dampen the reaction, and the third 35 extending through the floor 4 to the top of the accumulator jacket 18 to control a small flow of water to the jacket. A pressure gauge 36 on the manifold pipe 23 indicates the pressure head, while a temperature gauge 37 at the top of the stand pipe 26 indicates the water output temperature.

In operation of the submerged apparatus, ambient sea water continually flows through the manifold pipe 23 and the coil 21, picking up combustion heat in the reaction chamber 11. The heat is generated by the reaction of Al, $H_2O$ and NaOH. A small amount of water is tapped off from the manifold 23 through a needle valve 38 in the third branch pipe 35 to control the flow of NaOH into the reaction chamber 11. An important point is that the NaOH flow and the water flow through the manifold pipe 23 and the coil 21 are both subject to the same head pressure, so that first order effects which would change the water output temperature at the stand pipe 26 are avoided. Also, if the pump 24 fails, the flow of caustic soda into the reaction chamber 11 automatically stops. Hot water passes through the water hose 6 to the diver's suit 5 to heat the diver, and also passes through the radiator 10 which heats the compartment 2.

If the reaction temperature increases unduly, it can be brought under control by opening an on-off valve 39 in the second branch pipe 34 so as to dump cold water into the reaction chamber 11 and force hot water, NaOH, $H_2$ and $NaAlO_2$ out through the venting tube 19. Said on-off valve 39 is also used to shut the reaction down at the end of a dive and before the submersible leaves the water.

The disc 20 closing the bottom safety opening acts as the final safety device on temperature runaway. Upon melting of the disc 20, sea water is sucked through the opening by the "air-lift" effect of hydrogen gas exiting at the top of the chamber 11, and quickly damps the runaway reaction. A large open ball valve (not shown) may be provided at the outside of the disc 20 to enable the reaction to be restarted if necessary. Alternatively, extra discs may be provided.

The reaction used in this embodiment is:

$$2Al + 2NaOH + 2H_2O \rightarrow 2NaAlO_2 + 3H_2$$

yielding about 93 k cal of heat per gram-molecule, or about $2\frac{1}{2}$ kW of heat energy per pound of aluminium. The reaction chamber 11 holds nine three-kilo and two one-kilo ingots 14, giving a total of 29 kilos or 63.8 lbs. of aluminium. The accumulator 16 is sized accordingly plus a 20% overage. This arrangement delivers nearly 160 kW-hours of heat energy, but with insulation and heat-exchanger losses, this reduces to something over 150 kW-hours of usable energy. In the North Sea, 18 kW is enough to provide a minimum comfortable flow of warm water to a diver, and 1 kW is about the amount needed to maintain a suitable ambient temperature in the diver lock-out compartment. Thus the 150 kW of this embodiment is enough to heat the compartment for the normal 8-hour mission duration, plus 6 hours of diver lock-out time, plus $1\frac{1}{2}$ days of emergency heating capability (including the heat production of the divers themselves).

Advantageous features of this embodiment are:

(a) The venting tube 19 at the top of the reaction chamber 11 vents the hydrogen gas, and at the same time restricts the interchange of caustic soda and seawater.

(b) The safety disc 20 at the bottom end 13 of the reaction chamber 11, when combined with (a) above, results in an airlift sucking-in seawater when the disc fails, or a dumping of liquids through the bottom end if the submersible is out of the water.

(c) The coupling together of the head pressures on (i) the water flow through the coil 21 in the reaction chamber 11 and (ii) the flow of caustic soda into the reaction chamber, resulting in an automatic coupling together of heat supply and demand.

(d) The manual over-ride and shutdown features of the valve in the second branch pipe 34.

(e) The use of surrounding water to dampen the reaction in the event that the reaction temperature is too high.

(f) In the event of clogging of the system by reaction products ($NaAlO_2$), water may be introduced by the valve 39 in the second branch pipe 34 to dissolve the highly soluble $NaAlO_2$ and force it out through the venting tube 19. In that case, the venting tube 19 is made larger, is insulated, and is concentric around the stand pipe 26 for a few feet adjacent to the reaction chamber 11, so as to act as an exchanger which puts the heat taken out in the venting tube 19 back into the circuit.

For circumstances where the system is primarily required to provide emergency heat in a hull it is possible to omit altogether the source of electrical power from the hull.

Thus a second embodiment of the invention, referring now to FIG. 2, the apparatus consists of (a) a submersible vessel hull 1 having therein a diver lock-out compartment 2 with an opening 3 in the floor 4 thereof for passage of a diver, (b) heat generating means 45 mounted exteriorly on the hull, and (c) heat exchanging means including a system of fins 46 mounted interiorly on the hull, to provide radiative and convective transfer of heat from the heat generating means 45 to the compartment 2 by means of a heat-conductive intermediate partition 47 between the heat generating means 45 and the fins 46.

The heat-generating means 45 include exteriorly of the hull 1 and mounted thereon a heat insulated reaction chamber 48, the top of which is provided with an upright venting tube 49 to release gaseous reaction products from the reaction chamber 48 into the ambient water W.

A central feed-through aperture 50 in the bottom is closed by a disc 51 which melts at a critical temperature (in the order of 190° F.). A wire screen 55 covers the aperture 50 and the disc 51. A caustic soda accumulator (not shown) is provided as in the first embodiment and caustic soda is driven to a reaction zone 52 containing aluminium ingots 53 by a hand crank (not shown) interior of the hull, operating a peristaltic pump (not shown) on the exterior of the hull 1 to pump sea water into the caustic soda accumulator as before. Heat insulating material 54 envelopes the hull 1 and heat generating means 45.

Heat transfer is thus direct rather than via water and heat exchangers. For fine temperature control in the hull, removable insulation panels (not shown) may be used to lower the transfer of heat, and of course more caustic soda is added to increase the heating effect.

In place of the safety disc of the reaction chamber a snap-action bi-metallic element may be used which automatically reseats upon cooling of the reaction zone.

In this way the apparatus may be used as an emergency heater capable of supplying heat for several days as required but requiring no electricity for its operation.

By combining the apparatus of the first and second embodiments to form a composite apparatus, the temperature of the atmosphere in the compartment 2 may be controlled by covering and uncovering the fins 46 (FIG. 2) to vary the convective exchange, whilst the temperature in the reaction chamber 41 (FIG. 1) is controlled to suit the needs of the diver(s).

I claim:

1. In submersible apparatus for use in underwater operations, which includes a hull to house personnel, heat generating means associated with the hull which has (a) a reaction chamber defining therein a reaction zone for chemical reactants cpable of reacting together exothermically and producing a gaseous by-product;

(b) means for introducing reactants to the reaction zone; and (c) means for venting the gaseous by-product from the reaction chamber; the improvement comprising valve means through which water may be drawn by the "air-lift" effect of exiting gas through the venting means wherein the valve means comprises a portion of the reaction chamber which defines an aperture and a valve member which is adapted to close the aperture and which is operable to open the aperture at a predetermined temperature to enable entry of water to the reaction zone and/or dumping of reaction zone contents on reaction runaway, the water being drawn into the reaction zone through the aperture by the "air-lift" effect of gas exiting through the venting tube.

2. The submersible apparatus of claim 1 wherein the venting means is a venting tube extending from the top of the reaction chamber to discharge gas into the ambient water.

3. The submersible apparatus of claim 1 wherein the valve means is a metal disc whose melting point is below a predetermined danger level of temperature liable to be reached under conditions of reaction runaway.

4. The submersible apparatus of claim 3 wherein a large open ball valve is provided at the outside of the disc to enable the reaction to be restarted.

5. The submersible apparatus of claim 1 wherein the means for introducing reactants includes, for introducing a liquid reactant, an accumulator of the separated type adjacent to the reaction chamber, which accumulator has one side connected to water supply ducting and the other connected to the reaction chamber so that pressure of water supplied to one side forces liquid reactant by compression out the other into the reaction zone.

6. The submersible apparatus of claim 5 wherein the accumulator is a jacket and bladder accumulator.

7. The submersible apparatus of claim 1, including liquid heating means having a heat exchanger in the reaction chamber.

8. The submersible apparatus of claim 7, wherein the reaction chamber is of upright generally cylindrical form with the reaction zone in the lower portion thereof, and the heat exchanger is an upright helical tube disposed in the chamber above the reaction zone.

9. The submersible apparatus of claim 7, wherein the heat generating means are on the hull exteriorly thereof and the heating means include means for supplying water under greater than ambient pressure through the heat exchanger to the hull interior.

10. The submersible of claim 9, wherein the heating means include a pump for location in the cold water outside the hull, supply ducting extending from the pump through the hull interior to the heat exchanger inlet, and discharge ducting extending from the heat-exchanger outlet into the hull interior.

11. The submersible apparatus of claim 10, wherein the discharge ducting includes a stand pipe extending upwards from the heat-generating means and into the hull and connectible at its upper end to the upper end of a diver's hose to enable use of the heated water to heat a diving suit.

12. The submersible apparatus of claim 10 or 11, wherein a branch pipe extends from the supply ducting in the hull to the hull exterior, and a valve is provided in the branch pipe to enable adjustment of the head pressure and water flow through the heating system.

13. The submersible apparatus of claim 10 wherein a second branch pipe extends from the supply ducting in the hull to the reaction zone in the reaction chamber, and a check valve is provided in the branch pipe to enable the introduction of cold water to the reaction zone so that the reaction is dampened and simultaneously combustion products are forced from the reaction chamber through the venting tube.

14. The submersible apparatus of claim 10 including a water radiator in the hull, a water supply line extending from the discharge ducting to the radiator inlet, and a water exhaust line extending from the radiator outlet and through the hull to discharge into the ambient water.

15. The submersible apparatus of claim 14, wherein the water exhaust line comprises a heat-exchanging helical coil enclosing a portion of the supply ducting extending between the hull and the heat-exchanger inlet and has a heat-insulating housing mounted on the reaction chamber and enclosing the helical coil.

16. The submersible apparatus of claim 1, wherein the heat generating means are in the interior of the hull.

17. The submersible apparatus of claim 16, wherein the reaction chamber and the hull abut one another, and the area of abutment forms a heat-conductive partition to enable heat-transfer to the hull interior.

18. The submersible apparatus of claim 17, wherein the reaction chamber and the hull are contained within a common insulating layer.

19. The submersible apparatus of claim 18, wherein reaction heat from the reaction chamber is conducted via the heat-conductive partition to a finned heat exchanger on the interior surface of the hull.

20. The submersible apparatus of claim 1 where said valve means comprises a bottom portion of the reaction chamber.

* * * * *